(12) United States Patent
Mazess et al.

(10) Patent No.: US 6,449,334 B1
(45) Date of Patent: Sep. 10, 2002

(54) INDUSTRIAL INSPECTION METHOD AND APPARATUS USING DUAL ENERGY X-RAY ATTENUATION

(75) Inventors: Richard B. Mazess, Madison; David L. Ergun, Verona, both of WI (US)

(73) Assignee: Lunar Corporation, Madison, WI (US)

( * ) Notice: Subject to any disclaimer, the term of this patent is extended or adjusted under 35 U.S.C. 154(b) by 1 day.

(21) Appl. No.: 09/675,224

(22) Filed: Sep. 29, 2000

(51) Int. Cl.[7] ............................................... G01N 23/06
(52) U.S. Cl. ........................................... 378/53; 378/58
(58) Field of Search ............................. 378/51, 53, 54, 378/56, 58

(56) References Cited

U.S. PATENT DOCUMENTS

| | | | |
|---|---|---|---|
| 2,992,332 A | 7/1961 | Madigan | 250/83.3 |
| 4,168,431 A | 9/1979 | Henriksen | 250/358 R |
| 4,504,963 A | 3/1985 | Johnson | 378/53 |
| 5,319,547 A * | 6/1994 | Krug et al. | 364/409 |
| 5,481,584 A * | 1/1996 | Tang et al. | 378/98.9 |
| 5,841,833 A * | 11/1998 | Mazess et al. | 378/98.9 |

OTHER PUBLICATIONS

Lehmann, L.A., Alvarez, R.E., Macovski, A. and Brody, W.R., Generalized Image Combinations in Dual KVP Digital Radiography, Med. Phys 8(5), Sep.–Oct. 1981, pp. 659–667.

* cited by examiner

Primary Examiner—Robert H. Kim
Assistant Examiner—Jurie Yun
(74) Attorney, Agent, or Firm—Quarles & Brady LLP

(57) ABSTRACT

An industrial inspection device uses measurements at two x-ray energy to measure the relative proportions of two materials of a binary industrial composition by determining a mass ratio of a preselected selected first and second material expected to be in the binary composition and such as would provide a photoelectric absorption and Compton scattering consistent with the attenuation of the x-rays at the first and second energy. A relative proportion at different locations can be used to develop an image of one basis material. The image can be used to determine whether a product has an unacceptable composition or inclusions of foreign bodies.

18 Claims, 3 Drawing Sheets

INDUSTRIAL INSPECTION METHOD AND APPARATUS USING DUAL ENERGY X-RAY ATTENUATION

BACKGROUND OF THE INVENTION

The invention generally relates to the non-destructive analysis of industrial products and more particularly to using dual energy x-ray attenuation measurements to determine the composition of products in an industrial environment.

In industry it is often important to determine the composition of the product for purposes of quality control. Similarly, particularly in the food industry, it is important to locate contaminants or identify certain substances the quantity of which must be controlled. Moreover, it is desired to test the product without destroying it or altering its make-up in any way.

As one example, it is often important to determine the fat and bone content of cut or processed meat, since the price of meat is based largely on the amount of lean meat being sold. Also, processed meat may contain bone fragments or other objects from the sawing and boning process that could injure a consumer or otherwise substantially reduce the value of the meat.

Techniques of chemical analysis of industrial products, such as for determining the amount of fat in meat, are well known, but such laboratory techniques are time consuming and costly. Moreover, these techniques typically require that the product be physically or chemically broken down, consequently, only selected samples of the product can be analyzed, rather than each product. This diminishes the accuracy of the analysis since the quantities of substances and contaminants can vary from one product to another.

One non-destructive method of analyzing products uses x-ray or gamma radiation. For example, U.S. Pat. Nos. 2,992,332 and 4,168,431 describe systems detecting attenuation of x-rays passing through the product. Using such methods, each product rather than just samples, can be analyzed. Unfortunately, accurate x-ray attenuation determinations of compositions of matter require all other variable, particularly the density and total thickness of the sample to be precisely controlled.

U.S. Pat. No. 4,504,963 suggests that the need for careful product sample preparation (to ensure constant density and thickness) can avoided by using at least three separate x-ray beams, each operating at a different energy level. According to the application, the multiple x-ray beams each provide a different attenuation value and thus provide a "signature" that may be empirically related to a particular composition, regardless of slight density or thickness variations in the product. This approach, if feasible, thus avoids the problems inherent in preparing uniform product samples for testing. Nevertheless, it requires both multiple measurements of the product at various densities and thicknesses so as to deduce the signature ranges. Further, there is no indication that a unique signature will be available for products other than meat.

There is a need for a simple method for rapidly determining the composition of products without the need for careful sample preparation and that works over a range of different products.

BRIEF SUMMARY OF THE INVENTION

The present inventors have recognized that dual energy x-ray analyses, developed originally for medical imaging, can be used to make industrial composition measurements of irregular samples. The dual energy technique provides an indication of relative proportions of different materials that make up a composition largely indifferent to total material mass or density of the composition. Thus careful preparation of the samples is not required. Further, the theoretical basis of this imaging technique allows any two materials exhibiting different electron densities and atomic numbers to be distinguished.

Specifically then, the present invention provides a method of non-destructive analysis of binary industrial compositions including a first step of selecting a first and second basis material expected to compose the binary industrial composition. A beam of x-ray radiation having first and second energies is then generated and the binary industrial compositions are inserted into the beam such that the beam traverses an arbitrary mass of the portions varying between compositions. The attenuation of the x-ray beam after passage through the binary industrial compositions at the first and second energy is then detected and from this, a relative proportion defining a mass ratio of the selected first and second material is deduced such as would provide a photoelectric absorption and Compton scattering consistent with the attenuation of the x-rays at the first and second energy. Data is then output to a user indicating this relative proportion.

Thus it is one object of the invention to make use of a modeling of Compton scattering and photoelectric absorption to cancel out effects caused by varying thicknesses, densities, and inhomogeneities in the measured material and in this way provide a flexible industrial measuring tool applicable to a wide variety of material where extensive sample preparation is impractical.

The method may include the further step of deducing from the attenuation of the x-rays at the first and second energy, the total mass traversed by the beam. This mass may be output or used with the relative proportion to output masses of the first and second material.

Thus it is another object of the invention to provide total mass value in addition to the proportions of two basis materials in a binary industrial composition. The same modeling process that allows the measurement of proportion to be indifferent to the quantity of the material to be measured allows the quantity to be deduced. This total mass value can provide additional information useful, for example, in combining relative proportion measurements for different samples in a mass weighted average.

The x-ray beam may be operated on a continuous basis as the binary industrial compositions are moved through the beam along a path, and the path length during which the binary industrial compositions are moved through the beam may be measured to producing a total composition mass as a time integral of the total mass traversed by the beam. In this regard, a conveyor holding the binary industrial compositions may perform movement of the compositions and the conveyor may include a sensor providing a measure of path length of movement of the binary industrial compositions. The binary industrial compositions may be constrained in extent perpendicular to the beam axis and the path such that the constrained extent lies wholly within the beam.

Thus it is another object of the invention to allow quantitative assessment of a loosely aggregated binary industrial composition. By constraining the composition only to lie within the beam width without regard to height or length, the composition can be fully characterized as it passes through the beam.

Creating the x-ray beam may make use of two x-ray tubes, each providing different x-ray energy. The two x-ray tubes may be operated at different voltages and/or be filtered using different filters. Two separate x-ray detectors may be used to measure the attenuations at the two energies with each x-ray tube directing a beam to a different one of the detectors. The x-ray detectors may optionally be preferentially sensitive to a different one of the first and second x-ray energy.

Thus it is another object of the invention to greatly simplify the manufacture of a device for dual energy industrial inspections by using two x-ray tubes and possible dedicated detectors that may be optimized for their one particular energy measurement.

An image of a first basis material image based upon the proportion determined at different points through the binary industrial compositions may be developed and used for monitoring the presence of foreign bodies of the first basis material.

Thus it is another object of the invention to provide material selective images such as may be used to improve conventional machine vision techniques for the detection of foreign bodies in industrial products.

The foregoing and other objects and advantages of the invention will appear from the following description. In this description, reference is made to the accompanying drawings which form a part hereof and in which there is shown by way of illustration preferred embodiments of the invention. Such embodiments do not necessarily represent the full scope of the invention, however, and reference must be made therefore to the claims for interpreting the scope of the invention.

DETAILED DESCRIPTION OF THE PREFERRED EMBODIMENTS

Figure 1:
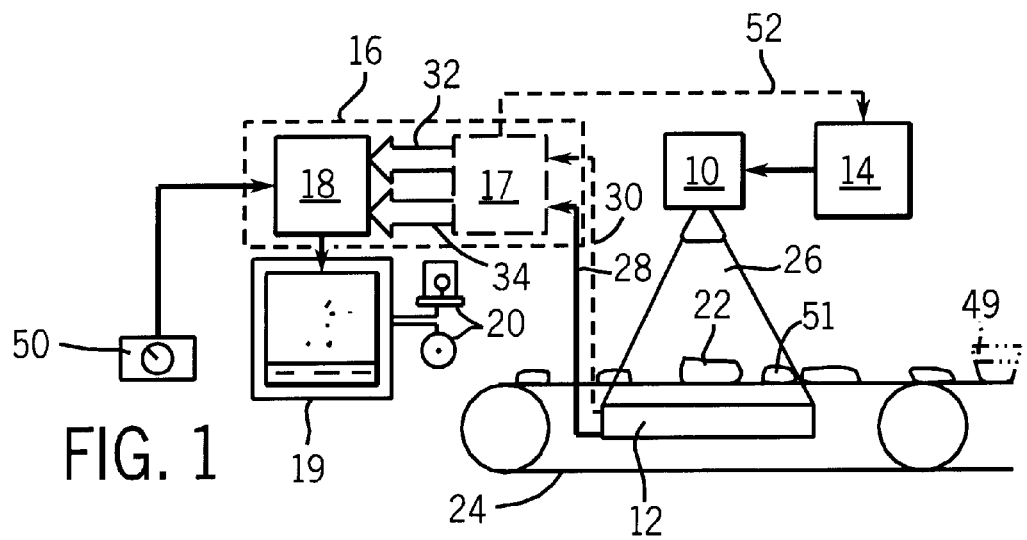
FIG. 1 is schematic representation of the dual energy industrial inspection device of the present invention in which industrial products are analyzed as they move along a conveyor.

Referring to FIG. 1, an industrial inspection device according to a first embodiment of the invention, includes an x-ray tube 10, a radiation detector 12, a power supply 14, a computer 16 having an energy discriminator 17 and a modeler 18, a video display 19 and an alarm 20. In stationary versions of the present invention shown in FIGS. 1 and 4, binary industrial compositions 22 are supported on a conveyor belt 24 that runs between the x-ray tube 10 and radiation detector 12 to intersect an x-ray beam 26 emitted from the x-ray tube 10. In a portable version of the invention shown in FIGS. 6 and 7, individual binary industrial compositions 22 are set into and supported by a receiving cradle (described below) positioned between the x-ray tube 10 and the radiation detector 12 so as to intersect the x-ray beam 26.

The inspection device of the present invention uses dual energy x-rays to selectively determine composition data and image substances and foreign bodies without regard to variations in the size or mixture of the binary industrial compositions 22. Dual energy refers to radiation at two or more bands of energy, emitted simultaneously or in succession, or as part of a broadband of polyenergetic radiation over the diagnostic imaging range. As is known in the art, the measurement of x-ray energy attenuated by an object in two distinct energy bands can be used to determine information about the photoelectric absorption and Compton scattering of the particular materials of the object. Photoelectric absorption and Compton scattering are determined by the electron density and atomic number of the materials and are functions of the x-ray energy. Accordingly, with two measurements of the object and two different energies, a proportion of two predefined materials of a composition can be identified. The mathematics and theory of this process is described in the paper "Generalized Image Combinations In Dual KVP Digital Radiography", Lehmann, et. al. Med. Phys. 8(5) September/October 1981, hereby incorporated by reference.

It is important to note that a by-product of this calculation is that the total quantity of material measured is factored out and hence this measurement process is particularly suited for industrial applications where the measured produce varies in thickness, density or is highly inhomogeneous. It is important, too, to note that the existence of only two attenuation mechanisms of Compton scattering and photoelectric absorption means that additional measurements at third or fourth x-ray energies provide no new information in this method. Techniques using more than two energy measurements, insofar as they are different from the present modeling approach, may not produce this same benefit of eliminating sample mass effects.

The binary industrial compositions 22 may include a wide variety of manufactured or processed goods that may be approximated as being binary compositions having only two distinct materials that attenuate x-rays differently. For example, lumber, paper products, plastic products, and foodstuffs to the extent that they can be characterized as binary compositions (e.g., water and wood) are industrial products that may be analyzed with the present invention.

For clarity, the following description describes the industrial inspection system as used to analyze composition and detect foreign bodies in processed meat samples, which will be designated in the figures by the numeral 22. Nevertheless, the invention should not be considered limited to meat and it should be understood that the meat could be replaced by other binary industrial combinations. In this application, the present invention uses dual energy x-ray techniques to analyze meat as either of the binary compositions of bone/meat or fat/meat so that the bone or fat content can be imaged and in the latter case, the leanness of the meat can be calculated.

Referring to FIG. 1 in a first embodiment, the x-ray tube 10 is energized on a periodic or continuous basis and high and low energy x-rays are produced either by switching voltages on the x-ray tube 10 or by filtering the polyenergetic beam with a kedge filter or the like as is understood in the art. The dual energy x-rays are detected by the detector 12 after passing through the meat 22 and the conveyor 24. The detector 12 may be energy discriminating, for example, using a stacked or side-by-side detector design known in the art in which different detector elements are filtered to be preferentially sensitive to different x-ray energies or may be a pulse height discriminating detector such as scintillation detectors or may be an energy indifferent detector synchronously switched with changes in x-ray tube voltage.

The x-ray detector 12 provides a set of high and low energy measurements through line 28 at multiple pixel locations over a detector area within the x-ray beam 26. The multiple locations may be derived through the use of a linear or array-type detector or a scanning detector having one or a few detector elements.

The computer 16 receives electrical signals from the detector 12. Specifically, they are received at a dual energy discriminator 17 which receives the detection signals from line 28 to produce a high energy attenuation signal 32 and a low energy attenuation signal 34 for each of many pixels over the area of the x-ray detector 12. The discriminator 17 which may be implemented as a program executed by the computer 16 or a specific hardware being part of computer 16 operates differently depending on the particular method of creating and detecting the dual energy x-rays. In the case of the switched voltage system, the discriminator 17 controls the switching via line 52 to synchronously decode the electrical signals on line 28 as either high or low energies. With a pulse height discriminating system, the discriminator 17 uses well known threshold techniques to segregate and count signals on line 28 as high or low energy x-ray photons. With stacked or side-by-side detectors, the high and low energy signals are carried over separate lines.

The high energy attenuation signal 32 will generally be the log of the ratio of the high energy signal detected by the x-ray detector 12 with the meat sample 22 within the x-ray beam 26 divided by the full intensity of the high energy beam 26 as detected by x-ray detector 12 absent an intervening object. The logarithm reflects the fact that attenuation is an exponential function, the amount of attenuation depending on the flux of radiation passing through the material. Likewise the low energy attenuation signal 34 will be the logarithm of the ratio of the low energy signal received by the x-ray detector 12 with the meat sample 22 in position divided by the low energy signal received by the x-ray detector 12 without the meat. Additional correction factors may be introduced to accommodate gain and offset variations of individual detector elements as well as the effects of x-ray beam hardening as is well known in the art.

The high and low energy attenuation signals 32 and 34 are then received by the modeler 18 which combines them pixel by pixel to produce a leanness measurement or an image 36 that may be displayed on display 19. When a single leanness measurement is to be produced, the modeler 18 can independently average the attenuation values of the two energy levels over all pixels. To achieve a more accurate image or measurement, the total attenuation value of each energy level can be weighted according to the thickness of the meat sample 22 (determined by the raw attenuation of the high or low energy) or the location of each pixel. Thus, for example, measurements corresponding to the center and thicker portion of the meat sample 22 could be given a higher weighting than those corresponding to the thinner edges.

Figure 2:
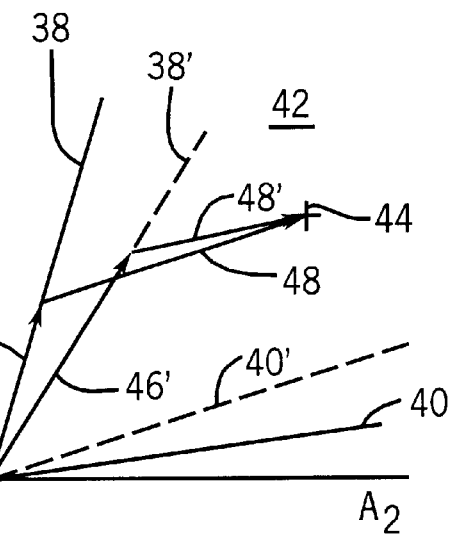
FIG. 2 is a schematic representation of a modeling process employed in the industrial inspection device of FIG. 1.

Referring now to FIG. 2, two basis materials 38 and 40 may be defined and represented as lines extending at a fixed slope through an origin of basis material plane 42 whose axes A1 and A2 are arbitrarily defined to contain all the energy information in the dual energy x-ray measurement. A1 and A2 may but need not be high and low energy attenuation as calculated above. The basis materials are preselected as expected components of a binary industrial composition. The angle of the lines of basis materials are a function of the atomic number and electron density of the particular basis material as per the convention established in the Lehmann paper described above. The length of lines in the basis material plane 42 represents the amount of the particular basis material in the sample.

For each pixel detected by the detector 12 containing information at two energies taken along a ray through the meat sample 22, a pixel value 44 may be plotted in the basis material plane 42. This pixel value 44 may be decomposed into the two basis materials 38 and 40 by laying vector lines 46 and 48 along parallels to the lines of basis materials 38 and 40 to sum to the pixel value 44. Thus, if basis material 38 is bone and basis material 40 is meat, the magnitude of vector 46 indicates the amount of bone in the meat sample 22 along the ray of the pixel, whereas the magnitude of vector 48 indicates the amount of meat along the same ray. A similar vector analysis can be conducted for discerning the fat content in the meat sample 22. This process deduces from the attenuation of the x-rays at the first and second energy, a relative proportion defining a mass ratio of the selected first and second material such as would provide a photoelectric absorption and Compton scattering consistent with the attenuation of the x-rays at the first and second energy. Note that modeling of the basis material amounts according to their photoelectric absorption and Compton scattering does not require that photoelectric absorption and Compton scattering be calculated directly or output to the user. Rather this modeling is inherent in the methodology described above including a priori selection of two basis materials and recognition of the sufficiency of only two energy measurements to uniquely distinguish those two basis materials.

Figure 3:
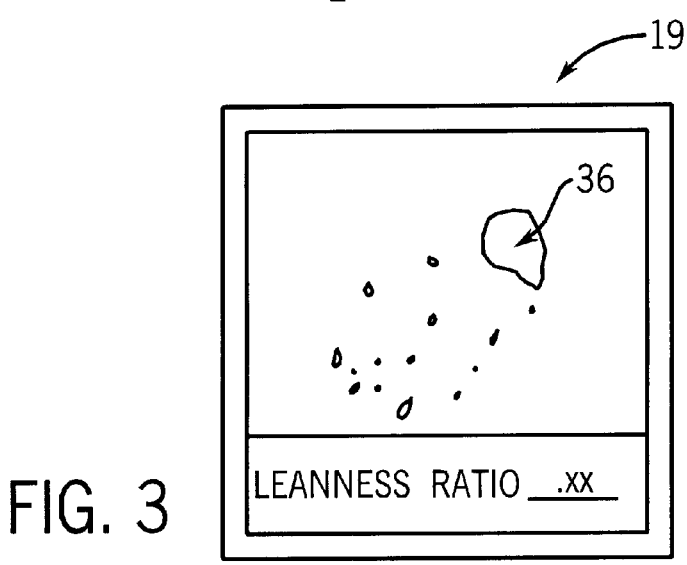
FIG. 3 is an enlarged view of a foreign body image display of the industrial inspection device of FIG. 1.

Referring to FIGS. 2 and 3, a bone-only image may be produced by using the magnitude of vector 46 for each pixel value 44 to define the intensity of a corresponding pixel on the image 36 of the display 19 and discarding the information of vector 48. Conversely, a meat image (not shown) may be produced by using the magnitude of vector 48 as the determinate for the image pixel intensities and discarding the information of vector 46.

Referring again to FIG. 1, an operator control 50 may be provided to set the slope of the lines for basis materials 38 and 40 (and hence the composition of the basis materials). Thus, for example, basis material 38 may be changed to a different basis material 38' having a lesser sloped line and basis material 40 may be changed to a different basis material 40' having a greater sloped line. In this case, the relative magnitudes of the vectors 46' and 48' (corresponding to previous vectors 46 and 48) change mirroring the new selection of basis materials. Thus, this permits the operator to easily tune the modeler 18 so as to discriminate between fat and meat, rather than bone and meat. Referring to FIG. 3, the fat content can be calculated and displayed in any suitable manner, such as a leanness ratio (which may be a unit-less value) or as a color-coded image (not shown). This ratio is indifferent to the magnitude of the vectors 46 and 48. Alternatively or in addition, the sum of the magnitudes of the vectors 46 and 48 may be determined (using vector addition) to deduce the total material (mass) of the sample. This mass may be applied to the ratio of the materials to determine a mass for each material.

In the event that the binary industrial composition is disposed on the conveyor 24 in a semi-continuous stream, the total mass of the product, the total masses of the binary components or a proportion of the binary components weighted by total mass may be determined by monitoring the motion of the conveyor 24 using a well known position sensor system and integrating the total mass signal or the total mass signal times the proportion of the binary components over conveyor distance moved. The conveyor 24 may include side walls to keep the product loosely aggregated within the beams 26 in a direction across the path which the conveyor 24 moves.

Since the inspection device can be used for any suitable industrial product, tuning the combiner (changing the slope of the line) allows any two basis materials to be analyzed and imaged. Therefore, the inspection device can be used to analyze other foodstuffs such as alcoholic beverages (for water vs. alcohol), including beer, cider, wine and liquor, and dairy products, (for fat vs. non-fat) including yogurt, butter, margarine, cheese and ice cream. Preferably, liquid products are analyzed in a suitable container 49, as shown in phantom in FIGS. 1 and 4, which can be end product packaging or other processing containers.

Moreover, the industrial inspection device may be used to determine the water composition of industrial products such as wood, tobacco and dehydrated foods, or the ash content in wood, paper and coal. As yet another example, the inspection device of the present invention may be used to determine the amount of titanium oxide in paint.

This process may also be used to set the device for changes in the composition of the meat, such as when analyzing cut meat rather than processed meat. Thus, the meat sample 22 can be any type of cut or processed meat, including beef, chicken, pork, lamb, deer, turkey, game bird, fish and crustacean.

As with composition, foreign bodies or contaminants having low density, such as plastic chips, as well as high density foreign bodies, such as metal burrs and stones, can be detected in any suitable industrial product by setting one of the basis materials to the expected composition of the foreign body.

Referring again to FIGS. 1 and 4, preferably a calibration phantom 51 having a known composition and known x-ray attenuation characteristics is disposed within the range of the x-ray beam 26 and continuously or periodically scanned so that the computer can make a calibration measurement and adjust inaccurate measurements of the industrial products commonly caused by x-ray drift and system aging. Although not preferred, alternatively, the device may be recalibrated using known calibration procedures when studying a different parameter or when analyzing binary industrial compositions 22 having different physical or chemical properties.

As mentioned above, dual energy measurements can be generated by affecting either the x-ray source or the radiation detector. Specifically, the x-ray source can produce a polychromatic beam, with or without a k-edge filter to provide two energies simultaneously, or via a movable filter or by control of the voltage of an x-ray tube's power supply via input line 52 to provide two energies sequentially. Alternatively, dual energy measurements may be provided by using a conventional single or broad band energy x-ray with or without a k-edge filter but modifying the detector, e.g., detecting multiple energy thresholds or using multiple energy discriminating detectors that are selectively sensitive to one energy band. When a polychromatic beam is used, power supply control line 52 is not required.

Specifically, in a switched x-ray tube voltage system, the voltage supplied to the x-ray tube 10 is periodically changed from a high to a low voltage so as to shift the energy spectrum of the produced x-ray beam. The x-ray detector 12 may have polychromatic sensitivity to distinguish between high and low energy x-rays in synchrony with a switching of the filter or x-ray tube voltage under the control of line 52. In this case, a single time multiplexed signal is transmitted along line 28 and received by the dual energy discriminator 17 as described.

Alternatively, the radiation detector may have side-by-side detector elements with different energy sensitivities, or stacked detector elements in which high and low energy detecting elements are aligned along the axis of the x-rays 26. In either of these configurations, line 28 provides the low energy attenuation signal 34 and a second line 30 provides the high energy attenuation signal 32 and no energy discriminator 17 is needed.

Specifically, in the side-by-side arrangement, two rows of detector elements are placed side-by-side in an orientation perpendicular to the direction the meat samples 22 are traveling. The detector elements of the first row have different energy sensitivities from that of the second row, so that each row detects a different energy band. Alternatively, the detector elements may be configured in a checker-board pattern, such that within each row, and column perpendicular to each row, low and high energy detector elements alternate. Regarding the stacked detector, typically a front-most detector will measure total x-ray flux and a rearward detector will measure only higher energy x-ray photons not stopped by an intervening filter (not shown). Low energy photons may be deduced from the detected quantity of the total and high energy photons.

Figure 4:
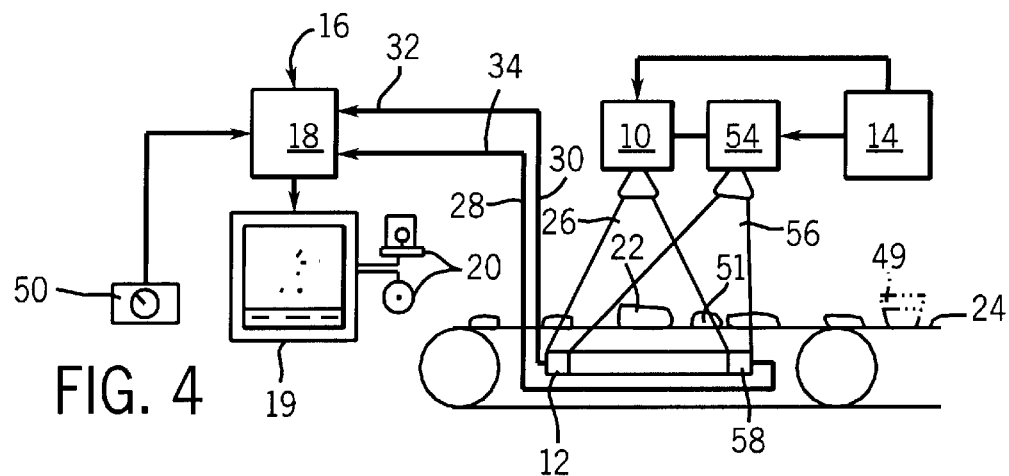
FIG. 4 is another embodiment of the present invention having two independent x-ray tubes emitting two x-ray beams, one at a high energy level and one at a low energy level.

Referring to FIG. 4, rather than filtering or switching tube voltage or using a polychromatic beam, the device may be configured to include a second x-ray tube 54. In this case, the first x-ray tube 10 receives high voltage for producing a high energy band x-ray beam and the second x-ray tube 54 receives lower voltage producing a lower energy x-ray beam 56. In a two tube system such as this, the device may also have a second detector 58, the two detectors each being sensitive to the respective energy bands of the emitted x-ray beams 26, 56. In this case, each detector 12, 58 provides a single energy attenuation signal, high energy attenuation signal 32 and one for low energy attenuation signal 34. Alternately, the device may have only the one detector 12, as described above, being energy discrimination for receiving both x-ray beams. In either case, the detector(s) can be any of the previously described types provided two attenuation signals are produced.

Referring to FIGS. 1 and 4, depending upon the x-ray tube/detector configuration for achieving dual energy attenuation, the x-ray tube 10 can be collimated to produce an area, cone, pencil or fan beam. The area beam is preferred because it requires little collimation, thus improving tube efficiency as known in the art. Moreover, since area beams are detected by an area of the detector, this arrangement provides the advantage of speed and high resolution.

Figure 5:
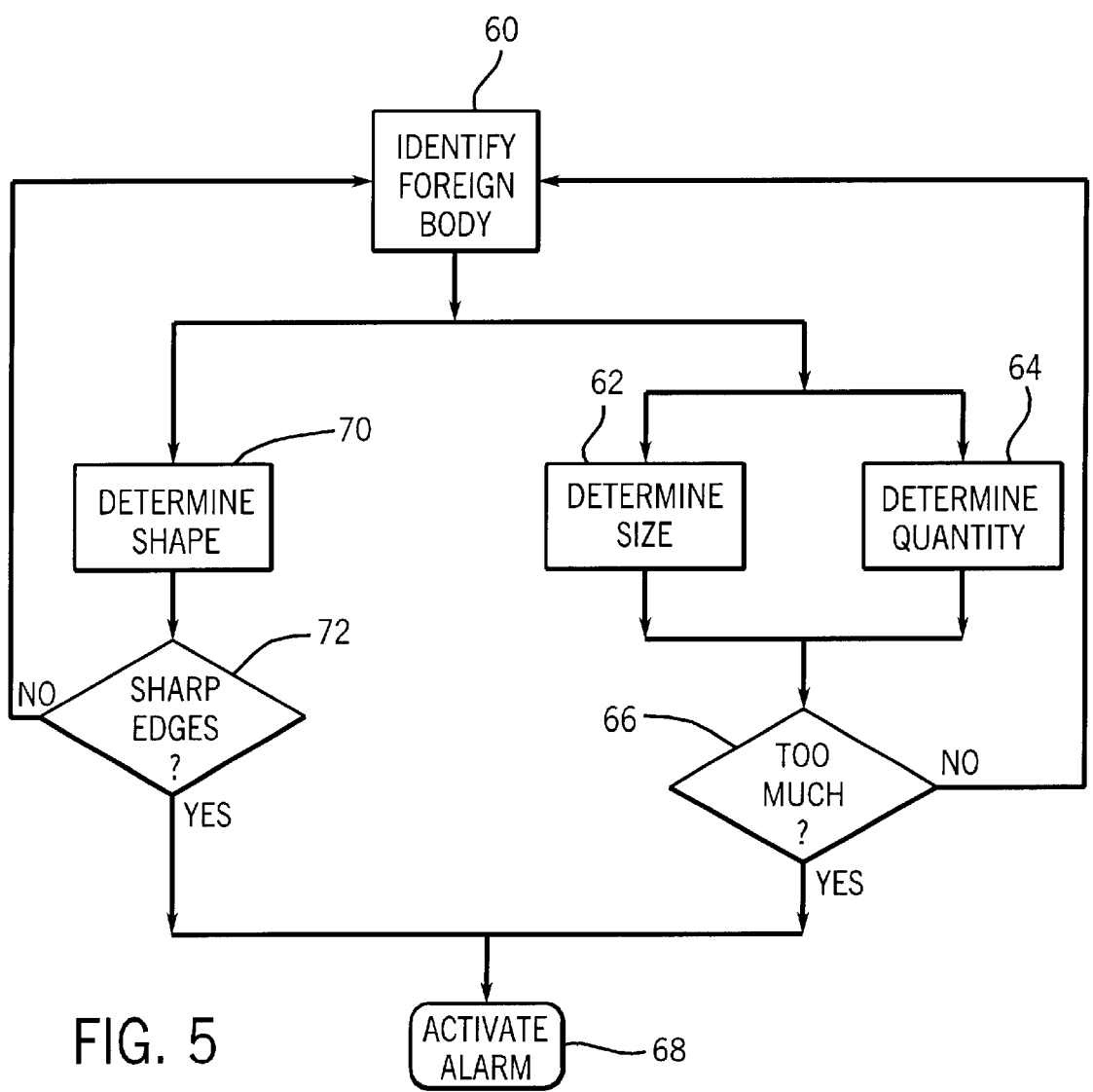
FIG. 5 is a flow chart showing the process steps for activating an operator alarm in the event the industrial product contains more than a pre-determined amount or size of foreign bodies.

FIG. 5 provides a process chart for signaling a line operator or test operator of an industrial product having foreign bodies that do not fall within predetermined acceptable safety or quality standards. For example, in the case of meat samples 22, the system can be adapted to activate the alarm 20, comprising conventional audio and visual signaling devices, if any bone fragment is detected, or if more than a predefined maximum quantity or bone mass is detected.

Also, the alarm 20 can be activated if bone fragments are detected that are too large or are dangerously jagged. The dual energy techniques described above are preferentially used to isolate the fragment, however, automatic detection of fragments may also be done with single energy systems.

This process begins at step 60 by identifying the bone using the above described dual x-ray attenuation process. Then at steps 62 and 64, the computer calculates the size and quantity of the detected bone fragments (or a general foreign body) of a selected basis material based upon the closed polygon formed by contiguous pixels corresponding to bone. The size may be total mass, total area, area of contiguous pixels representing a single body, area of contiguous pixels representing a single body as weighted by the mass of that basis material indicated at the pixels within that area. At step 66, if the calculated size and quantity values are higher than predetermined maximum values, the process advances to step 68, where computer 16 activates the alarm.

At step 70, contiguous pixels representing the bone fragments are also analyzed to determine the size or width of the edges of the bone fragments. Then at step 72, the edges are analyzed to determine whether they may cause injury if the bone fragment is inadvertently swallowed. This is done at step 72 by analyzing whether the bone fragment has any edges comprising less than a predetermined minimum amount of pixels over a predetermined minimum number of pixel rows. For example, an edge may be determined to be too sharp and jagged if it is less than 10 pixels wide for 50 or more rows of pixels. In such a case, the computer 16 activates the alarm 20 at step 68. If the alarm 20 is not activated for any reason, the process returns to step 60 to detect bone fragments in another meat sample 22.

Although the above describes activating the alarm 20 to notify an operator of bone fragments, it is also within the scope of the invention to activate the alarm 20 when detecting fat content to notify an operator that the fat content is outside an acceptable range of values, being either too high or too low.

Figure 6:
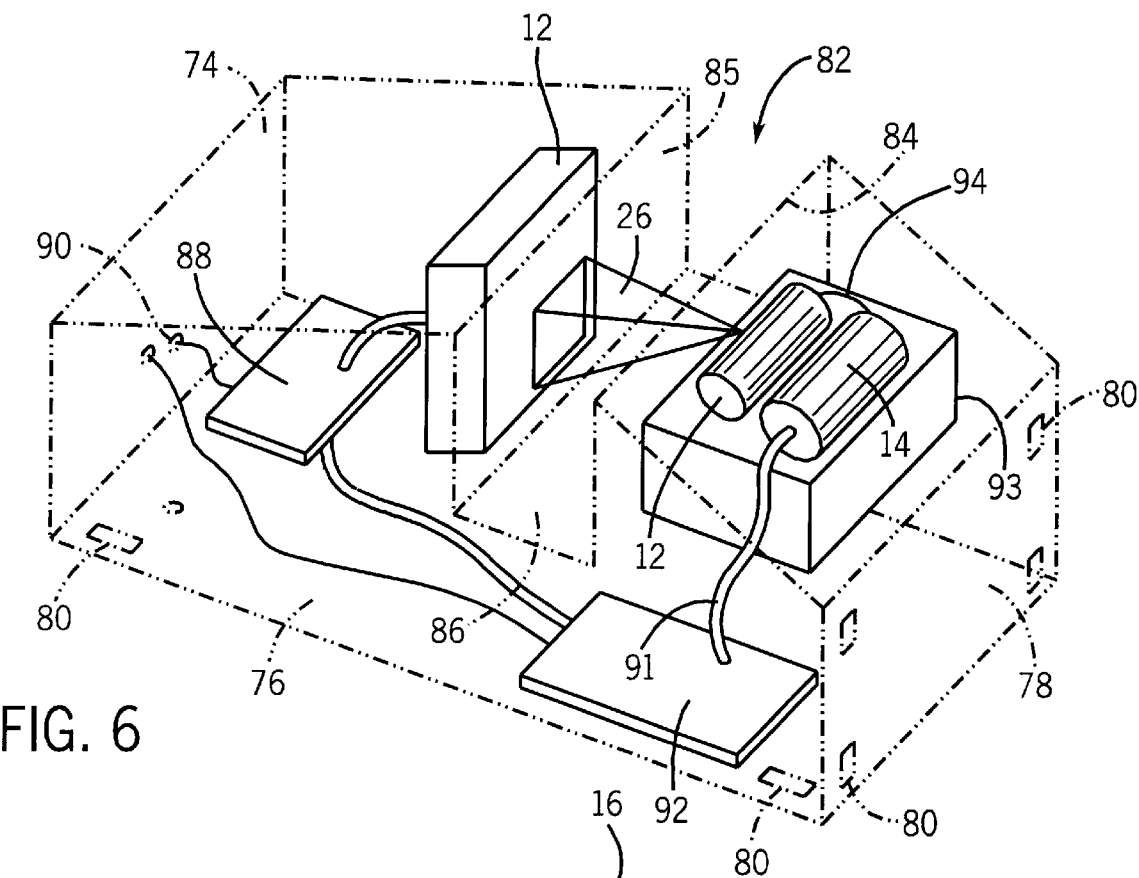
FIG. 6 is a perspective view of another embodiment of the present invention wherein the dual energy source and detector are contained in a compact housing.
Figure 7:
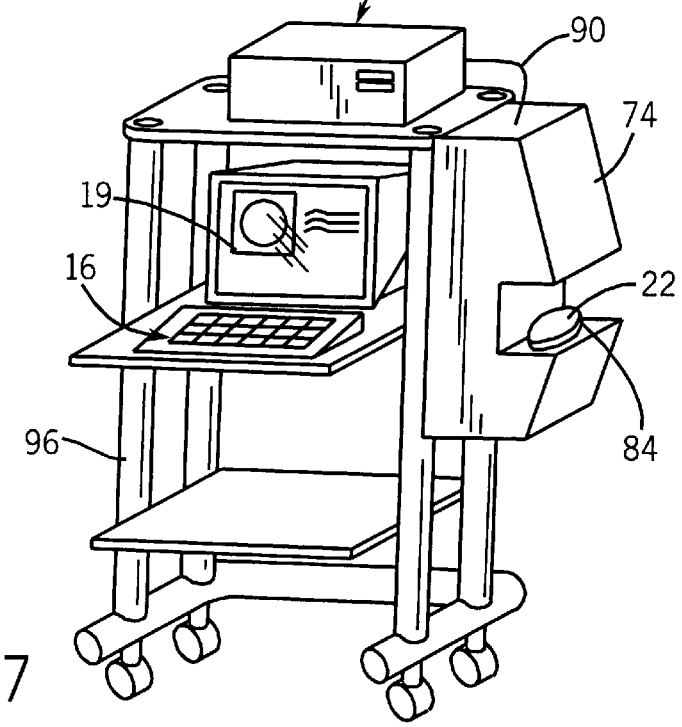
FIG. 7 is a perspective view of the embodiment of FIG. 6, showing the compact housing operatively connected to an external processor and image display and mounted to a portable structure.

Referring to FIGS. 6 and 7, a compact, portable embodiment of the present invention includes a housing 74 having a generally rectangular horizontal base 76 on which it may rest. Abutting the horizontal base 76 at one end is an upstanding secondary base 78 perpendicular to base 76 and also generally rectangular.

Each of the bases 76 and 78 include elastomeric feet 80 providing a cushioning between the base 76 or 78 when the housing is rotated to rest on base 76 or 78, with base 76 or 78, in turn, resting on a horizontal support surface such as the floor or a table.

A meat-receiving slot or cradle 82 extends inward to the housing 74 toward horizontal base 76 in a face of the housing 74 opposite the horizontal base 76. The slot 82 has walls 84 generally parallel to vertical base 78 and a bottom 86 generally parallel to horizontal base 76.

Within the housing 74 on one side of the slot 82 is the x-ray tube 10 projecting an area or cone x-ray beam through one wall 84 of the slot 82 and across the slot 82. The x-ray beam 26 passes through a second wall 85 of the slot 82 and is received by the x-ray detector 12 positioned within the housing 74 on the other side of the slot 82 from the x-ray beam 26. The x-ray tube 10 and detector 12 are fixed with respect to the housing 74.

A controller board 88 provides the image and measurement data from the detector 12 to an external connector 90 to a remote computer 16 for data processing. It will be understood, however, that the processing capability may also be contained on the controller board 88 and a self-contained display on the housing 74 may be used.

In this embodiment, the power supply 14 receives low voltage through leads 91 from a power supply board 92 that converts it to one of two higher voltage levels. Preferably, the x-ray tube 10 is a 'monoblock' configuration in which the high voltage x-ray power supply 14 and x-ray tube 10 are contained in a single rigid, insulating block 93. The block 93 has cavities bored within it to receive the tube 10 and power supply 14 and interconnecting high tension lead 94. A silica insulating compound is placed within the remaining portions of the cavity between the block 93, x-ray tube 10 and power supply 14. The insulating compound is amorphous, which permits expansion of these components due to heating and operation, but holds the components securely and protects them from shock.

The clear block 93 permits inspection of the internal components for electrical arcing and allows embedded instrumentation, such as for temperature and the like, to be placed proximate to the components of the x-ray tube 10 and power supply 14 yet viewed after assembly. The monoblock design simplifies calibration and replacement of the x-ray tube 10 and provides a short and fully enclosed high tension lead 94.

Referring now to FIG. 7, the compact embodiment of the invention may be mounted to a vertical wall or the side of a portable cart 96. Pegs (not shown) extending outwardly from the wall or cart 96 can be received within keyhole shaped sockets (not shown) in the base 76 of the housing 74. The cart 96 may hold the computer 16, which is connected to the controller board 88 (FIG. 6) by the external connector 90 and processes dual energy data according to the above-described techniques.

The above description has been that of preferred embodiments of the present invention. It will occur to those that practice the art that many modifications may be made without departing from the spirit and scope of the invention. For example, in any of the fixed or portable embodiments of the industrial inspection device, the liquid or solid industrial products may be loaded into containers 49, shown in phantom in FIGS. 1 and 4, having side walls that when filled define a constant, predefined thickness. This allows the apparatus to utilize a single energy beam without losing accuracy due to the affect variations in sample thickness have on single energy attenuation measurements. Moreover, in any embodiment, rather than analyzing discreet samples, the industrial products may be continuously conveyed between the x-ray source and detector to provide real-time monitoring during processing.

Accordingly, in order to apprise the public of the various embodiments that may fall within the scope of the invention, the following claims are made.

We claim:

1. A method of analyzing the composition of meat having an arbitrary fat content comprising the steps of:
   (a) identifying an index of photoelectric absorption and Compton scattering values corresponding to fat and non-fat meat;
   (b) generating a beam of x-ray radiation having first and second energies;
   (c) inserting meat samples of arbitrary size into the beam;
   (d) detecting an attenuation of the x-ray beam after passage through the meat samples at the first and second energies;
   (e) deducing from the index and the attenuation of the x-rays at the first and second energies a ratio of the non-fat meat and the fat; and
   (f) outputting data to a user indicative of the ratio.

2. The method of claim 1 including further the step of:
(e) deducing from the attenuation of the x-rays at the first and second energies the total mass traversed by the beam.

3. The method of claim 2 including further the step of:
(f) outputting the mass traversed by the beam.

4. The method of claim 2 including further the step of:
(f) outputting the masses of the fat and non-fat meat.

5. The method of claim 2 wherein the x-ray beam is operated on a continuous basis as the meat samples are moved through the beam along a path; and
including the further step (e) of measuring the path length during which the meat samples are moved through the beam and producing a total composition mass as a time integral of the total mass traversed by the beam.

6. The method of claim 5 wherein the step (c) is performed by a conveyor holding the meat samples and wherein the conveyor includes a sensor providing a measure of path length of movement of the meat samples.

7. The method of claim 1 wherein the meat samples are constrained in extent perpendicular to the beam axis and the path such that the constrained extent lies wholly within the beam.

8. The method of claim 1 wherein the x-ray beam is operated on an intermittent basis after each meat sample is inserted into the beam.

9. The method of claim 1 wherein the step (b) employs two x-ray tubes each providing a different x-ray energy.

10. The method of claim 9 wherein the two x-ray tubes are operated at different voltages.

11. The method of claim 9 wherein the two x-ray tubes are filtered using different filters.

12. The method of claim 9 wherein step (d) employs two separate x-ray detectors and each x-ray tube directs a beam to a different one of the detectors.

13. The method of claim 12 wherein each of the x-ray detectors is preferentially sensitive to a different of the first and second x-ray energies.

14. The method of claim 1, further comprising the step of:
(f) outputting a non-fat image based upon the ratio determined at different points through the meat samples.

15. The method of claim 1, further including the step of:
(f) outputting a leanness ratio of the non-fat meat to the meat sample.

16. The method of claim 15, wherein the user selects the index of photoelectric absorption and Compton scattering values utilized.

17. The method of claim 1, wherein the meat includes an arbitrary bone content, further comprising the steps of:
(g) identifying an index of photoelectric absorption and Compton scattering values corresponding to bone;
(h) deducing from the index and the attenuation of the x-rays at the first and second energies a second ratio of the bone and non-bone portions of the meat; and
(i) outputting a bone image based upon the second ratio determined at different points through the meat samples.

18. The method of claim 17 wherein the bone image is evaluated against a threshold selected from the group consisting of: a number of bone fragments, an area of bone fragment, an area of bone fragment times mass within that area, a shape of a bone fragment, and a total mass of bone.

* * * * *